United States Patent
Hsu et al.

(10) Patent No.: US 6,430,449 B1
(45) Date of Patent: *Aug. 6, 2002

(54) CATHETER FOR TREATING SUPRAVENTRICULAR TACHYARRHYTHMIAS

(75) Inventors: William Hsu, Circle Pines; Bruce H. KenKnight, Maple Grove, both of MN (US)

(73) Assignee: Cardiac Pacemackers, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/464,244

(22) Filed: Dec. 16, 1999

Related U.S. Application Data

(62) Division of application No. 09/044,284, filed on Mar. 19, 1998.

(51) Int. Cl.[7] ................................. A61N 1/05
(52) U.S. Cl. ........................................ 607/126
(58) Field of Search ................. 607/119, 122, 607/125, 126

(56) References Cited

U.S. PATENT DOCUMENTS

| 4,488,561 A | 12/1984 | Doring ........................ 128/786 |
| 4,641,656 A | 2/1987 | Smits ....................... 128/419 D |
| 5,111,811 A | 5/1992 | Smits ....................... 128/419 D |
| 5,165,403 A | 11/1992 | Mehra ...................... 128/419 D |
| 5,277,231 A | 1/1994 | Dostalek ....................... 140/106 |
| 5,396,902 A | 3/1995 | Brennen et al. ............. 128/772 |
| 5,411,524 A | 5/1995 | Rahul ............................. 607/4 |
| 5,439,006 A | 8/1995 | Brennen et al. ............. 128/772 |

(List continued on next page.)

Primary Examiner—William E. Kamm
(74) Attorney, Agent, or Firm—Schwegman, Lundberg, Woessner & Kluth, P.A.

(57) ABSTRACT

A system and method for treating atrial fibrillation using atrial pacing pulses to convert an atrial fibrillation to non-fibrillation atrial arrhythmia prior to delivering a low energy cardioversion/defibrillation shock. The system and method treats atrial fibrillations by first applying a plurality of pacing pulses to the atria which converts the atrial fibrillation to non-fibrillation atrial arrhythmia. Ventricular intervals are concurrently sensed and analyzed while the plurality of electrical pacing pulses are being applied. Upon detecting a period of stable ventricular intervals, the system then proceeds to deliver a low-energy cardioverting/defibrillating pulse of electrical energy across the atria of the heart.

24 Claims, 8 Drawing Sheets

U.S. PATENT DOCUMENTS

| | | | |
|---|---|---|---|
| 5,456,706 A | 10/1995 | Pless et al. | 607/122 |
| 5,476,498 A | 12/1995 | Ayers | 607/122 |
| 5,476,499 A | 12/1995 | Hirschberg | 607/123 |
| 5,545,204 A | 8/1996 | Cammilli et al. | 607/123 |
| 5,609,621 A | 3/1997 | Bonner | 607/122 |
| 5,617,854 A | 4/1997 | Munsif | 128/642 |
| 5,626,136 A | 5/1997 | Webster, Jr. | 128/642 |
| 5,662,119 A | 9/1997 | Brennen et al. | 128/772 |
| 5,683,431 A | 11/1997 | Wang | 607/28 |
| 5,683,445 A | 11/1997 | Swoyer | 607/125 |
| 5,759,202 A | 6/1998 | Schroeppel | 607/126 |
| 5,772,590 A | 6/1998 | Webster, Jr. | 600/374 |
| 5,772,693 A * | 6/1998 | Brownlee | 607/126 |
| 5,782,239 A | 7/1998 | Webster, Jr. | 128/642 |
| 5,797,967 A | 8/1998 | KenKnight | 607/4 |
| 5,824,031 A | 10/1998 | Cookston et al. | 607/122 |
| 5,843,153 A | 12/1998 | Johnston et al. | 607/122 |
| 5,849,032 A | 12/1998 | Van Venrooij | 607/123 |
| 5,853,426 A | 12/1998 | Shieh | 607/5 |
| 5,868,680 A | 2/1999 | Steiner et al. | 600/518 |
| 5,873,842 A | 2/1999 | Brennen et al. | 600/585 |
| 5,902,331 A | 5/1999 | Bonner et al. | 607/122 |
| 5,922,014 A * | 7/1999 | Warman et al. | 607/125 |
| 5,925,073 A * | 7/1999 | Chastain et al. | 607/125 |
| 5,951,471 A | 9/1999 | de la Rama et al. | 600/381 |
| 5,955,218 A | 9/1999 | Crespi et al. | 429/219 |
| 5,964,795 A | 10/1999 | McVenes et al. | 607/122 |
| 5,999,858 A | 12/1999 | Sommer et al. | 607/122 |
| 6,006,122 A | 12/1999 | Smits | 600/373 |
| 6,006,137 A | 12/1999 | Williams | 607/119 |
| 6,021,354 A | 2/2000 | Warman et al. | 607/123 |
| 6,070,104 A | 5/2000 | Hine et al. | 607/123 |
| 6,076,014 A | 6/2000 | Alt | 607/4 |
| RE36,765 E | 7/2000 | Mehra | 607/4 |
| 6,085,119 A | 7/2000 | Scheiner et al. | 607/122 |
| 6,096,064 A | 8/2000 | Routh | 607/9 |
| 6,115,628 A | 9/2000 | Stadler et al. | 600/517 |
| 6,115,630 A | 9/2000 | Stadler et al. | 600/521 |

* cited by examiner

CATHETER FOR TREATING SUPRAVENTRICULAR TACHYARRHYTHMIAS

CROSS-REFERENCE TO RELATED APPLICATIONS

This application is a division of U.S. patent application Ser. No. 09/044,284, filed Mar. 19, 1998, which is incorporated herein by reference.

TECHNICAL FIELD

The present invention relates generally to implantable medical devices and in particular to implantable electrical pulse generators for treating supraventricular tachyarrhythmias.

BACKGROUND OF INVENTION

Effective, efficient ventricular pumping action depends on proper cardiac function. Proper cardiac function, in turn, relies on the synchronized contractions of the myocardium at regular intervals. When the normal cardiac rhythm is initiated at the sinoatrial node, the heart is said to be in sinus rhythm. However, when the heart experiences irregularities in the coordinated contraction of the myocardium, due to electrophysiologic disturbances caused by a disease process or from an electrical disturbance, the heart is denoted to be arrhythmic. The resulting cardiac arrhythmia impairs cardiac efficiency and can be a potential life threatening event.

In the supraventricular region of the heart, electrophysiologic disturbances are called supraventricular tachyarrhythmias (SVT). SVT can take several distinguishable forms, including paroxysmal atrial tachycardia, atrial flutter, or atrial fibrillation. SVT are self-sustaining process and may be paroxysmal or chronic.

The mechanisms behind these conditions are not well understood, but, generally, the electrical impulses that normally cause sinus rhythm are thought to progress repeatedly around irregular conduction pathways within the heart. These conditions, if uncontrolled, can become life threatening if the aberrant electrical impulses enter the atrioventricular node (AV node) in a sporadic and/or at an accelerated rate and cause an irregular ventricular rate that degenerates into an immediate life threatening ventricular arrhythmia.

Physicians have typically relied on the use of either pharmacological agents and/or electrical techniques to control paroxysmal or chronic SVT. Many acute SVT patients convert to sinus rhythm after receiving treatment with pharmacological agents. However, antiarrhythmic pharmacological agents can have undesirable adverse effects, particularly if the need for drug therapy is chronic.

Alternatively, physicians have used various electrical techniques to treat SVTs. The SVT most frequently treated in this manner is atrial fibrillation. If the atrial fibrillation is acute, the physician may attempt an electrical cardioversion. This technique has been effective in converting atrial fibrillation, but it can be quite a painful experience for the patient. Implantable atrial cardioverters have also been suggested as a potential treatment for atrial fibrillation. However, the use of these devices can still subject the patient to a very painful and traumatic experience. Furthermore, the energy these devices deliver in attempting to treat atrial fibrillation has the potential for causing transient shock-induced dysfunction as well as permanent damage to the tissue near the cardioversion electrodes.

SUMMARY OF THE INVENTION

The present invention, in contrast, treats atrial fibrillation in a safe, effective, and more patient acceptable manner. The system of the present invention is unique in that it utilizes pacing level electrical energy impulses applied at a plurality of distinct locations within the supraventricular region of the heart to reduce the amount of electrical energy required to cardiovert or defibrillate the supraventricular region of the heart.

This lower energy method of treating a heart experiencing an atrial fibrillation reduces the potential for transient shock-induced dysfunction as well as permanent damage to the tissue near defibrillation coil electrodes. As a result, this method of treating a heart experiencing an atrial fibrillation is less painful and less traumatic to the patient as compared to the use of conventional implantable atrial cardioverters. Also, reducing the required energy could lead to further reductions in the size of the implanted device while extending battery life.

In one embodiment of the present invention, the system includes an implantable housing to which is releasably attached a first atrial catheter and a ventricular catheter. The first atrial catheter has a first atrial electrode and a first defibrillation electrode and is positioned within the heart with the atrial electrode and the first defibrillation electrode in a supraventricular region of the heart. The ventricular catheter has a first ventricular electrode, and is positioned within the heart with the first ventricular electrode in a right ventricular chamber of the heart.

The implantable housing also contains electronic control circuitry which is electrically connected to the first atrial electrode, the first defibrillation electrode, and the first ventricular electrode. The electronic control circuitry receives cardiac signals through the first atrial electrode and the first ventricular electrode, and delivers, upon detecting an atrial fibrillation, a plurality of pacing pulses to convert the atrial fibrillation to a non-fibrillation atrial arrhythmia such as atrial flutter.

In an additional embodiment, the first atrial catheter further includes at least a second atrial electrode and a second defibrillation electrode. The first atrial catheter is positioned within the supraventricular region of the heart with the first atrial electrode, the first defibrillation electrode and the second atrial electrode positioned within a coronary sinus vein of the heart, and the second defibrillation electrode within the right atrium chamber or major vein leading to the heart. In a further embodiment, the elongate body of the first atrial catheter has a series of lateral deflections that mechanically biases the first atrial electrode into physical contact with the coronary sinus vein of the heat.

The electronic control circuitry is electrically connected to the second atrial electrode and the second defibrillation electrode. The electronic control circuitry receives cardiac signals through the first and second atrial electrodes and the first ventricular electrode, and delivers, upon detecting an atrial fibrillation, a plurality of pacing pulses to convert the atrial fibrillation to a non-fibrillation atrial arrhythmia such as atrial flutter.

In an alternative embodiment, the system further includes at least a second atrial catheter, where the second atrial catheter has the second atrial electrode and the second defibrillation electrode, and is positioned within the heart with the second atrial electrode and the second defibrillation electrode in a supraventricular region of the heart. The electronic control circuitry is electrically connected to the second atrial electrode and the second defibrillation electrode. The electronic control circuitry receives cardiac signals through the first and second atrial electrodes and the first ventricular electrode, and delivers, upon detecting an atrial fibrillation, a plurality of pacing pulses to convert the atrial fibrillation to a non-fibrillation atrial arrhythmia such as atrial flutter.

Concurrent with the delivery of the plurality of pacing pulses, the system also senses and analyzes the ventricular rhythm to determine the stability of the ventricular intervals, where a ventricular interval is the time between the occurrence of sensed ventricular R-waves. In one embodiment, ventricular interval stability is determined from the variability of ventricular intervals sensed while the plurality of pacing pulses are being delivered. A stable ventricular interval has a variability value below a predetermined stability threshold value, and an unstable ventricular interval has a variability value that is greater than or equal to the predetermined stability threshold value.

During the delivery of the plurality of pacing pulses, if the system detects a period of stable ventricular intervals, it delivers a first level atrial shock to the heart. In one embodiment, the atrial shock is delivered between the first defibrillation coil and the implantable housing of the system, where the first defibrillation coil is located within the right atrium chamber of the heart or major vein leading to the right atrium chamber of the heart. In an alternative embodiment, the atrial shock is delivered between the first and second defibrillation coils, where the first defibrillation coil is located within the coronary sinus adjacent to the left atrium chamber of the heart and the second defibrillation coil is located within the right atrium chamber of the heart or a major vein leading to the right atrium chamber.

In an additional embodiment, if the plurality of pacing pulses does not convert the atrial fibrillation, the system repeats the steps of delivering a plurality of pacing pulses to the atria. As the system is repeating delivery of the plurality of pacing pulses it also concurrently senses and analyzes the stability of the ventricular intervals. Upon detecting stable ventricular intervals during the repeated plurality of pacing pulses, the system then proceeds to deliver the first level atrial shock to the heart to restore sinus rhythm. As a result, this method of terminating atrial fibrillation by first converting it to atrial flutter or some non-fibrillation atrial arrhythmia using pacing pulses then delivering a low-energy first level atrial shock to restore sinus rhythm provides for a less painful and a less traumatic experience for the patient.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments of the present invention illustrated herein are described as being included in an implantable heart cardioverter/defibrillator/pacemaker, which may include numerous pacing modes known in the art. The system and method of the present invention could also be implemented in an external cardioverter/monitor system.

Figure 1:
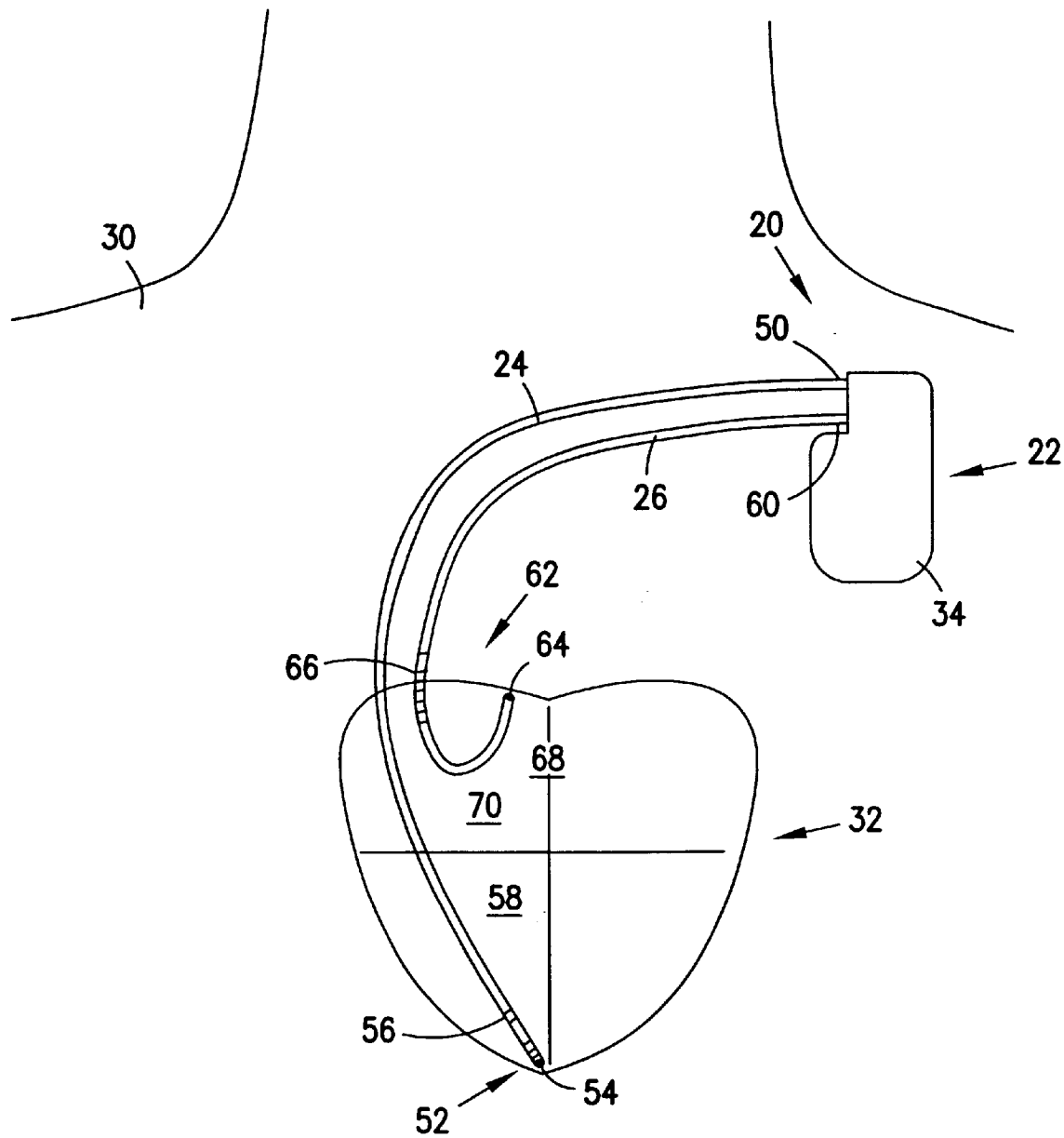
FIG. 1 is a schematic view of an atrial cardioverter/defibrillator with one embodiment of a first atrial catheter and a ventricular catheter implanted in a heart from which segments have been removed to show details.
Figure 2:
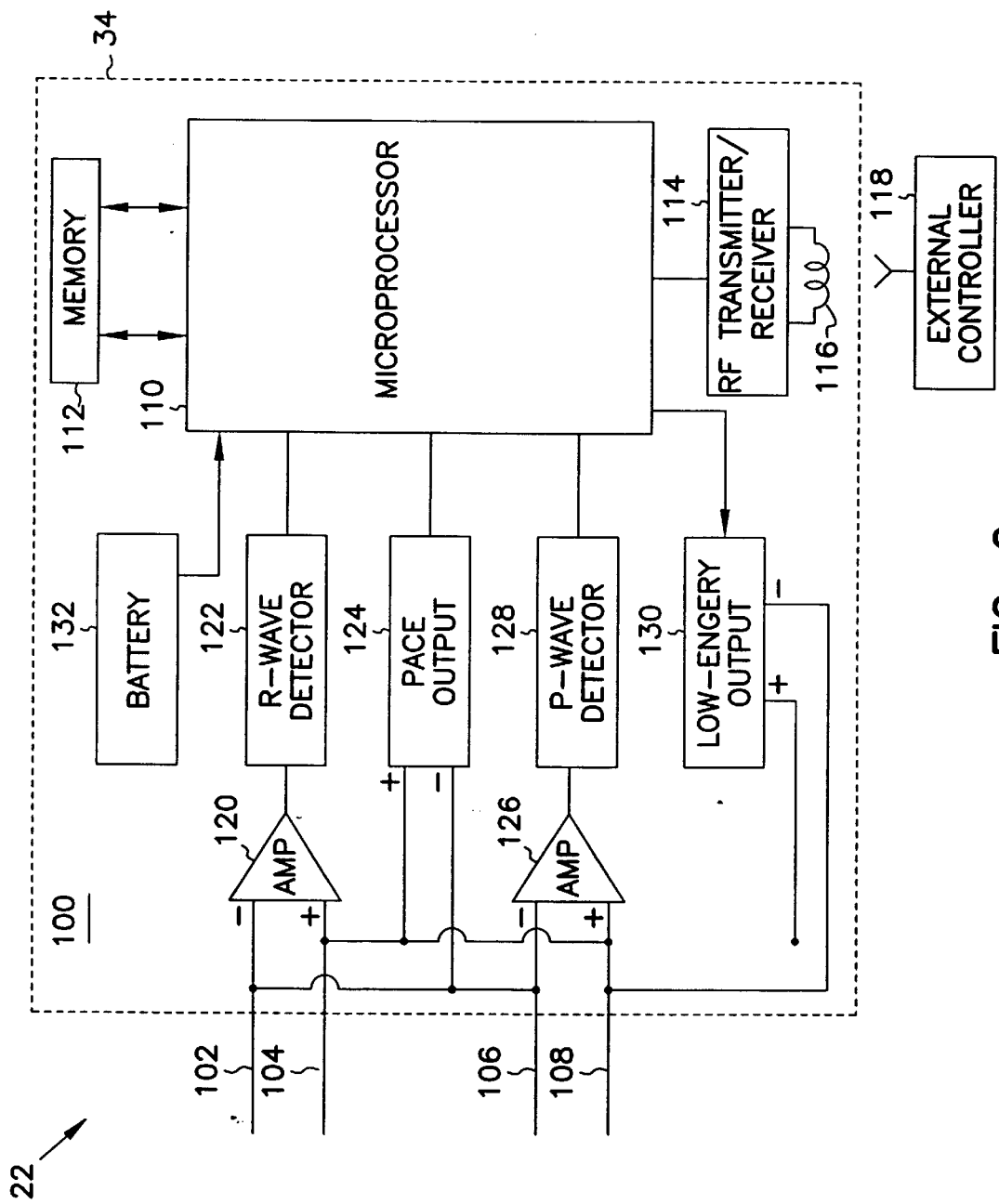
FIG. 2 is a block diagram of an atrial cardioverter/defibrillator according to one embodiment of the present invention.

Referring now to FIGS. 1 and 2 of the drawings, there is shown a system 20 including an atrial cardioverter/defibrillator 22 physically and electrically coupled to a ventricular catheter 24 and a first atrial catheter 26. The system 20 is implanted in a human body 30 with portions of the ventricular catheter 24 and the first atrial catheter 26 inserted into a heart 32 to detect and analyze electric cardiac signals produced by the heart 32 and to provide electrical energy to the heart 32 under certain predetermined conditions to treat supraventricular tachyarrhythmias, including atrial fibrillation, of the heart 32.

One embodiment of a schematic of the atrial cardioverter/defibrillator 22 electronics is shown in FIG. 2. The atrial cardioverter/defibrillator 22 comprises an implantable housing 34 which contains electronic control circuitry 100. The electronic control circuitry 100 includes terminals, labeled with reference numbers 102, 104, 106 and 108 for connection to electrodes attached to the surface of the ventricular catheter 24 and the first atrial catheter 26.

The ventricular catheter 24 is an endocardial lead adapted to be releasably attached to the implantable housing 34 of the atrial cardioverter/defibrillator 22. The ventricular catheter 24 has an elongate body with a proximal end 50 and a distal end 52 and is shown as having a first ventricular electrode 54 located at, or adjacent, the distal end 52 of the ventricular catheter 24. In one embodiment, the first ventricular electrode 54 is a tip electrode positioned at the distal end 52 of the ventricular catheter 24. Alternatively, the first ventricular electrode 54 is an annular, or a semi-annular ring electrode positioned adjacent the distal end 52. The first ventricular electrode 54 is electrically connected to terminal 102 and to the electronic control circuitry 100 through an electrically insulated conductor provided within the elongate body of the ventricular catheter 24.

In an additional embodiment, the ventricular catheter 24 further includes a second ventricular electrode 56. The second ventricular electrode 56 is an annular, or a semi-annular ring electrode electrically connected to terminal 104 and to the electronic control circuitry 100 through an electrically insulated conductor provided within the elongate body of the ventricular catheter 24. The second ventricular electrode 56 is spaced apart and proximal from the first ventricular electrode 54 such that when the ventricular catheter 24 is positioned within the heart 32 the first ventricular electrode 54 and the second ventricular electrode 56 reside within a right ventricle 58 of the heart 32, with the first ventricular electrode 54 in an apex location within the right ventricle 58.

The first atrial catheter 26 is an endocardial lead adapted to be releasably attached to the implantable housing 34 of the atrial cardioverter/defibrillator 22. The first atrial catheter 26 has an elongate body with a proximal end 60 and a distal end 62 and is shown as having a first atrial electrode 64 located at, or adjacent, the distal end 62. In one embodiment, the first atrial electrode 64 is a tip electrode positioned at the distal end 62 of the first atrial catheter 26. Alternatively, the first atrial electrode 64 is an annular, or a semi-annular ring electrode positioned adjacent the distal end 62. The first atrial electrode 64 is electrically connected to terminal 106 and to the electronic control circuitry 100 through an electrically insulated conductor provided within the elongate body of the first atrial catheter 26.

The first atrial catheter 26 also includes a first defibrillation electrode 66 which is connected to terminal 108 and to the electronic control circuitry 100 through an electrically insulated conductor provided within the elongate body of the ventricular catheter 24. In one embodiment, the first defibrillation electrode 66 is a defibrillation coil electrode as are known in the art. The first defibrillation electrode 66 is spaced apart and proximal from the first atrial electrode 64 such that when the first atrial catheter 26 is positioned within the heart 32 the first atrial electrode 64 and the first defibrillation electrode 66 are positioned within a supraventricular region 68 of the heart 32.

In one embodiment of the present system, the first atrial catheter 26 is positioned within the supraventricular region 68 of the heart 32 with the first atrial electrode 64 and the first defibrillation electrode 66 positioned within the right atrium chamber 70 of the heart 32 or a major vein leading to the right atrium chamber 70 of the heart 32. In one embodiment, the first atrial catheter 26 is positioned within the right atrium chamber 70 with the distal end 62 positioned within the right atrial appendage such that the first atrial electrode 64 make physical contact with the right atrium chamber 70 of the heart 32 and the first defibrillation electrode 66 is positioned within the right atrium and/or major vein leading to the right atrium chamber 70.

The atrial cardioverter/defibrillator 22 is a programmable microprocessor-based system, with a microprocessor 110 and a memory 112, which contains parameters for various pacing and sensing modes. Microprocessor 110 includes means for communicating with an internal controller, in the form of a RF receiver/transmitter 114. This includes a wire loop antenna 116, whereby it may receive and transmit signals to and from an external controller 118. In this manner, programming commands or instructions are transferred to the microprocessor 110 of the atrial cardioverter/defibrillator 22 after implant In one embodiment operating data is stored in memory 112 during operation. This data may be transferred to the external controller 118 for medical analysis.

In the atrial cardioverter/defibrillator 22 of FIG. 2, the first ventricle electrode 54 and the second ventricular electrode 56 are coupled to a sense amplifier 120, whose output is shown connected to an R-wave detector 122. These components serve to sense and amplify the QRS waves of the heart, and apply signals indicative thereof to the microprocessor 110. Among other things, microprocessor 110 responds to the R-wave detector 122 by providing pacing signals to a pace output circuit 124, as needed according to the programmed pacing mode. Pace output circuit 124 provides output pacing signals to terminals 102 and 104, which connect to the first ventricular electrode 54 and the second ventricular electrode 56, for ventricular pacing.

The first atrial electrode 64 and the first defibrillation electrode 66 are coupled to a sense amplifier 126, whose output is connected to a P-wave detector 128. These components serve to sense and amplify the P-waves of the cardiac cycle from the region of the right atrium chamber 70, and apply signals indicative thereof to the microprocessor 110. Among other things, microprocessor 110 responds to the atrial signals from the sense amplifier 126 applied to the P-wave detector 128 by providing pacing signals to the pace output circuit 124, as needed according to the programmed pacing mode. Pace output circuit 124 provides output pacing signals to terminals 106 and 108, which connect to the first atrial electrode 64 and the first defibrillation electrode 66, for normal atrial pacing and atrial pacing according to the present invention.

The microprocessor 110 also responds to the cardiac signals sensed within the heart 32 using the catheters 24 and 26 by providing signals to a low-energy output circuit 130 to provide low-level cardioversion/defibrillation electrical energy to the heart as needed according to the method of the present invention. Power to the atrial cardioverter/defibrillator 22 is supplied by an electrochemical battery 132 that is housed within the atrial cardioverter/defibrillator 22.

The electronic control circuitry 100 receives cardiac signals through the ventricle electrodes 54 and 56, the first atrial electrode 64 and the first defibrillation electrode 66, and upon detecting an atrial fibrillation, first delivers a plurality of pacing pulses to the heart to convert the atrial fibrillation to a non-fibrillation atrial arrhythmia, such as atrial flutter or non-fibrillation supraventricular arrhythmia, and then delivers a low-energy atrial shock once the ventricular intervals stabilize.

In the embodiment shown in FIG. 1, the ventricular catheter 24 and the electronic control circuitry 100 are utilized for bipolar sensing of the ventricular R-wave intervals and the ventricular rate of the heart 32. Bipolar pacing is delivered between the first and the second ventricular electrodes 54 and 56. In an alternative embodiment, the ventricular catheter 24 has only a first ventricular electrode 54. Sensing ventricular R-wave intervals and ventricular rate is then accomplished through unipolar sensing between the first ventricular electrode 54 and an exposed electrically conductive portion of the implantable housing 34 which has been coupled to the sensing amplifier 120. Similarly, unipolar pacing is applied to the heart 32 between the first ventricular electrode 54 and the conductive implantable housing 34.

Referring again to FIG. 1, the first atrial catheter 26 and the electronic control circuitry 100 are utilized for bipolar sensing within the supraventricular region 68, where bipolar signals from the right atrium chamber 70 are sensed between the first atrial electrode 64 and the first defibrillation electrode 66. Bipolar pacing is delivered between the first atrial electrode 64 and the first defibrillation electrode 66. In an alternative embodiment, unipolar pacing and sensing are provided from the first atrial catheter 26 between the first atrial electrode 64 and a conductive implantable housing 34.

The atrial cardioverter/defibrillator 22 further includes the low-energy output circuit 130, which operates under the control of the microprocessor 110. The low-energy output circuit 130 is connected to the first defibrillation electrode terminal 108, which connects to the first defibrillation electrode 66, and the conductive implantable housing 34. In this manner, defibrillation pulses are delivered between the first defibrillation electrode 66 and the implantable housing 34 when called for by the microprocessor 110.

Figure 3:
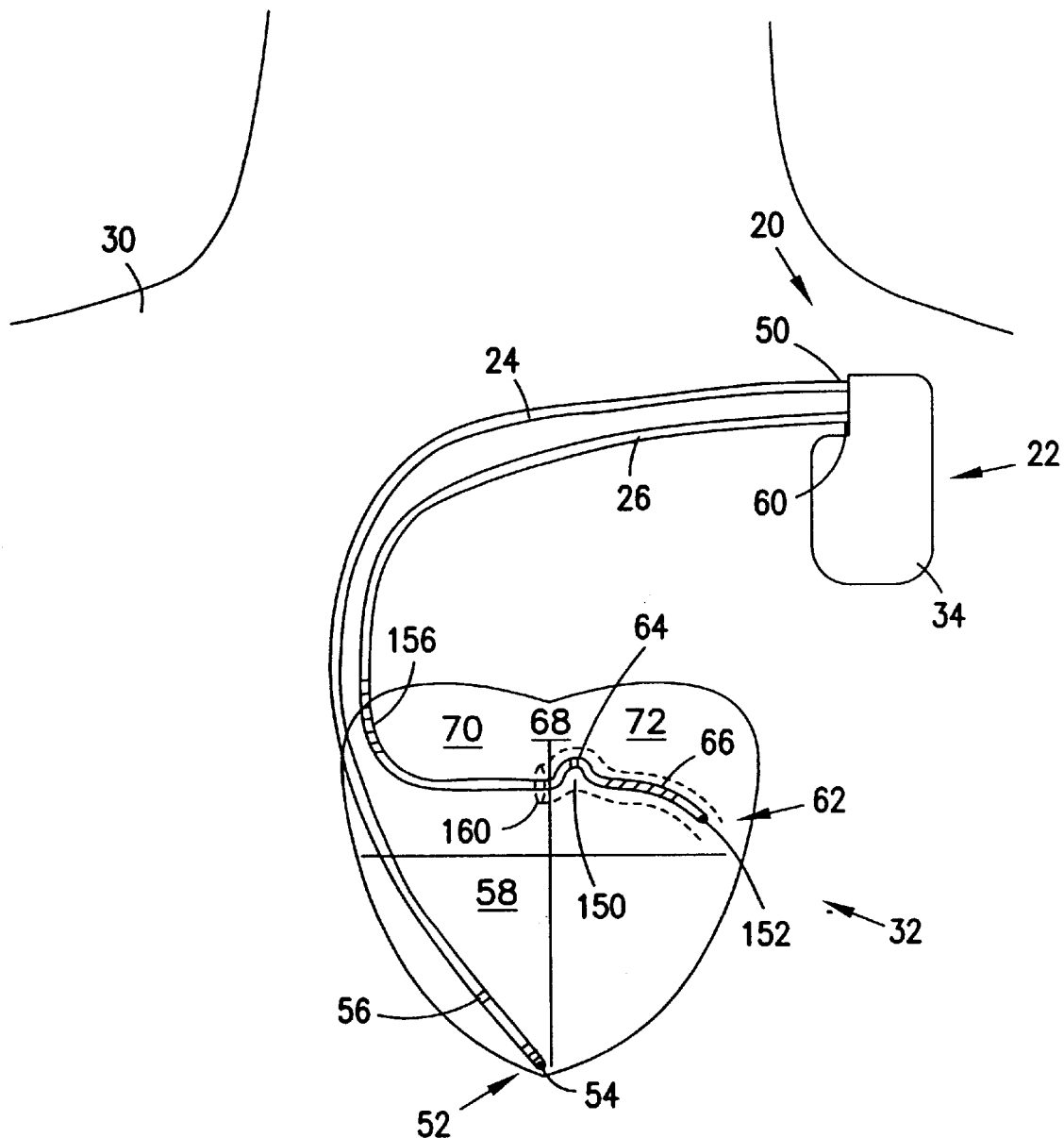
FIG. 3 is a schematic view of an atrial cardioverter/defibrillator with one embodiment of a first atrial catheter and a ventricular catheter implanted in a heart from which segments have been removed to show details.
Figure 4:
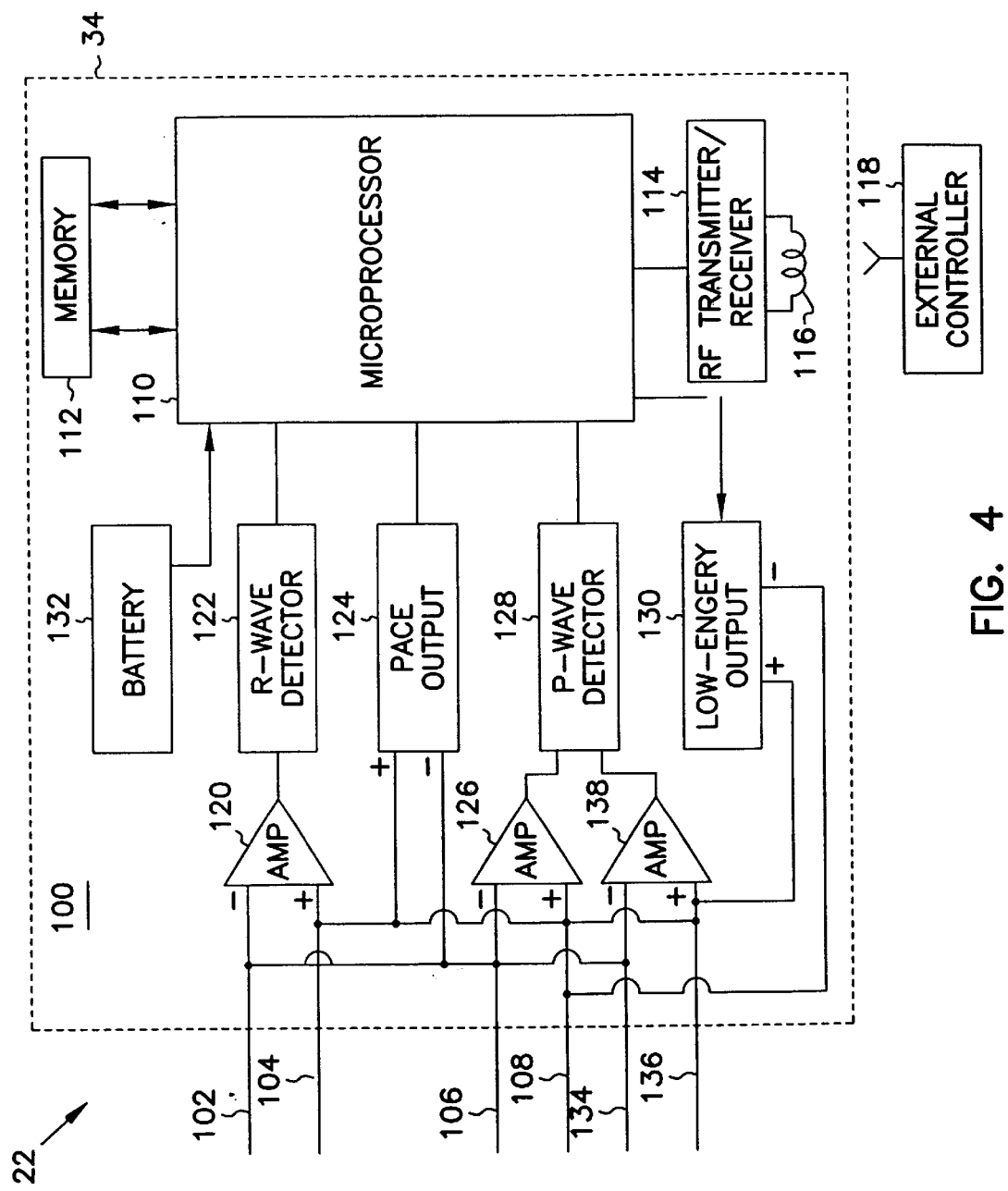
FIG. 4 is a block diagram of an atrial cardioverter/defibrillator according to one embodiment of the present invention.
Figure 5:
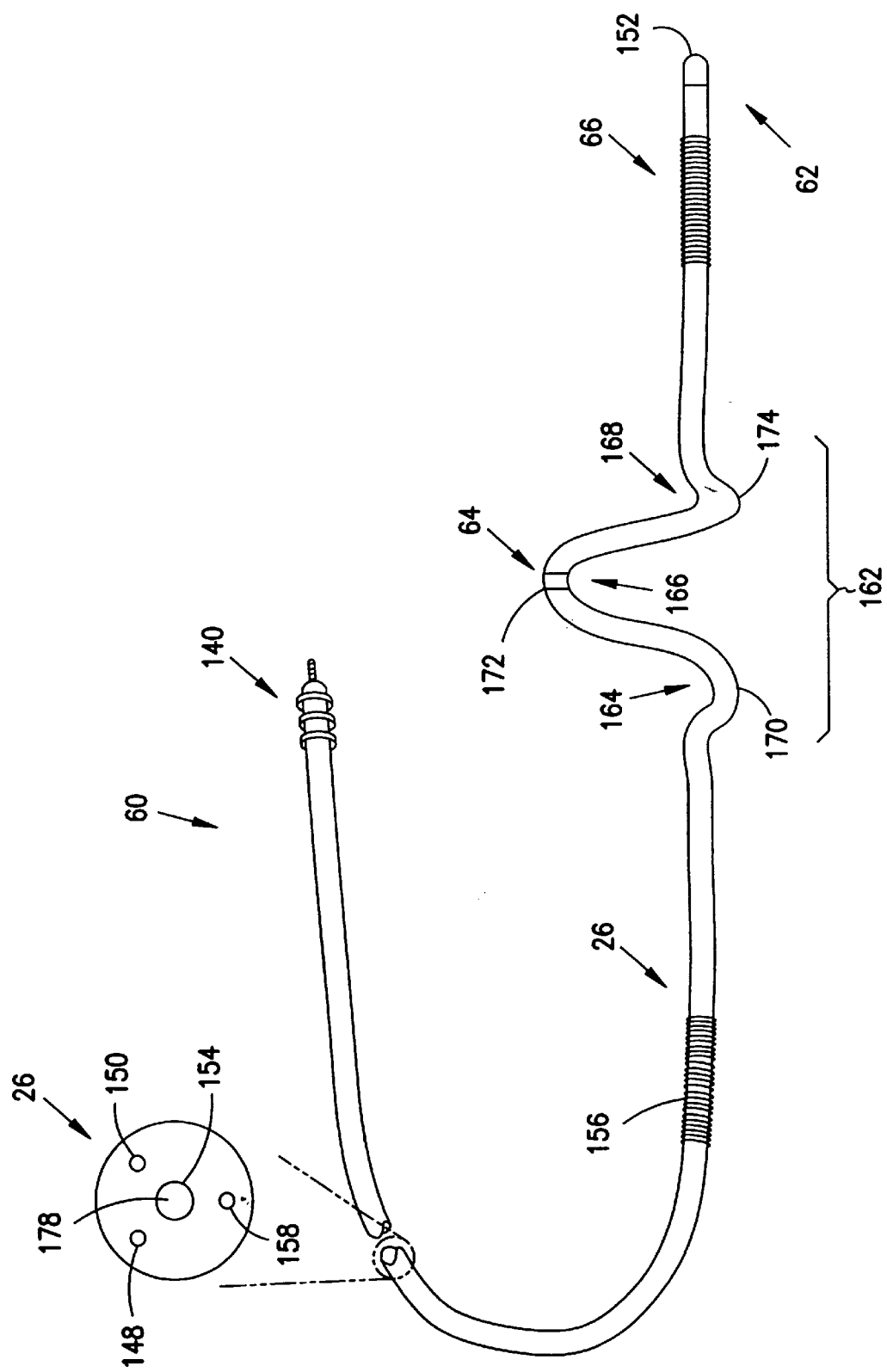
FIG. 5 is a schematic view of one embodiment of a catheter according to the present invention.

Referring now to FIGS. 3, 4 and 5, there is shown an alternative embodiment of the system 20 including the atrial cardioverter/defibrillator 22 physically and electrically connected to an alternative embodiment of the first atrial catheter 26. The system 20 is implanted in the human body 30 with portions of the ventricular catheter 24 and the first atrial catheter 26 inserted into the heart 32 to detect and analyze electric cardiac signals produced by the heart 32 and to proved electrical energy to the heart 32 under certain predetermined conditions to treat supraventricular tachyarrhythmias, including atrial fibrillation, of the heart 32.

Referring now to FIG. 4 there is shown an additional embodiment of the schematic of the atrial cardioverter/defibrillator 22 electronics. The atrial cardioverter/defibrillator 22 comprises an implantable housing 34 which contains electronic control circuitry 100. The electronic control circuitry 100 includes terminals, labeled with reference numbers 102, 104, 106, 108, 134 and 136 for connection to electrodes attached to the surface of the ventricular catheter 24 and the first atrial catheter 26.

The first atrial catheter 26 is an endocardial lead adapted to be releasably attached to the implantable housing 34 of the atrial cardioverter/defibrillator 22. The first atrial catheter 26 has an elongate body with a proximal end 60 and a distal end 62. In one embodiment, the first atrial catheter 26 has a connector terminal 140 at the proximal end 60 for attaching the proximal end 60 of the elongate body to the implantable housing 34 of the atrial cardioverter/defibrillator 22.

In one embodiment, the first atrial catheter 26 is shown as having a first atrial electrode 64 located between the proximal end 60 and the distal end 62 of the elongate body. In one embodiment, the first atrial electrode 64 is an annular, or a semi-annular ring electrode positioned on the elongate body of the first atrial catheter 26. The first atrial electrode 64 is electrically connected to terminal 106 and to the electronic control circuitry 100 through a contact end located at the proximal end 60 which is coupled to an electrically insulated conductor 148 extending longitudinally within the elongate body of the first atrial catheter 26.

In an additional embodiment, the first atrial catheter also includes a first defibrillation electrode 66 which is connected to terminal 108 and to the electronic control circuitry 100 through a contact end located at the proximal end 60 which is coupled to an electrically insulated conductor 150 extending longitudinally within the elongate body of the first atrial catheter 26. In one embodiment, the first defibrillation electrode 66 is a defibrillation coil electrode as are known in the art. The first defibrillation electrode 66 is spaced apart and longitudinally on the peripheral surface of the elongate body from the first atrial electrode 64 such that when the first atrial catheter 26 is positioned within the heart 32 the first atrial electrode 64 and the first defibrillation electrode 66 are positioned within a supraventricular region 68 of the heart 32.

The first atrial catheter 26 further includes a second atrial electrode 152 located on the elongate body of the first atrial catheter 26 and is spaced apart and longitudinally on the peripheral surface of the elongate body of the first atrial catheter 26. In one embodiment, the second atrial electrode 152 is spaced distally from the first atrial electrode 64 and the first defibrillation electrode 66 to position the second atrial electrode 152 at, or adjacent, the distal end 62 of the elongate body. In one embodiment, the second atrial electrode 152 is a tip electrode positioned at the distal end 62 of the first atrial catheter 26. Alternatively, the second atrial electrode 152 is an annular, or a semi-annular ring electrode positioned adjacent the distal end 62. The second atrial electrode 152 is electrically connected to terminal 134 and to the electronic control circuitry 100 through a contact end located at the proximal end 60 which is coupled to an electrically insulated conductor 154 extending longitudinally within the elongate body of the first atrial catheter 26.

The first atrial catheter 26 also further includes a second defibrillation electrode 156 which is connected to terminal 136 and to the electronic control circuitry 100 through a contact end located at the proximal end 60 which is coupled to an electrically insulated conductor 158 extending longitudinally within the elongate body of the first atrial catheter 26. In one embodiment, the second defibrillation electrode 156 is a defibrillation coil electrode as are known in the art. The second defibrillation electrode 156 is spaced apart and proximal from the first atrial electrode 64 such that when the first atrial catheter 26 is positioned within the heart 32 the first and second atrial electrodes 64 and 152, and the first and second defibrillation electrodes 66 and 156 are positioned within a supraventricular region 68 of the heart 32.

In one embodiment, the first atrial catheter 26 is positioned within the supraventricular region 68 of the heart 32 with the distal end 62 positioned within the coronary sinus vein 160 such that the first atrial electrode 64 is adjacent to and in physical contact with a portion of the left atrium chamber 72 of the heart 32 and the first defibrillation electrode 66 is positioned within the coronary sinus vein 160. In an additional embodiment, the second atrial electrode 152 is positioned within the coronary sinus vein of the heart 32 and the second defibrillation electrode 156 positioned within the right atrium chamber 70, or some major vein leading to the right atrium chamber 70 of the hear. 32.

The first atrial electrode 64, the second atrial electrode 152, the first defibrillation electrode 66 and the second defibrillation electrode 156 are arranged on the elongate body of the first atria catheter 26 in any combination or subcombination of electrodes. For example, in one embodiment the first defibrillation electrode 66 is positioned at or proximal to the distal end of the first atrial catheter 26. The first atrial electrode 64 is spaced apart and proximal from the first defibrillation electrode 66 to position the first atrial electrode 64 within the coronary sinus vein 160 or within the great cardiac vein. The second atrial electrode 152 is spaced apart and proximal from the first atrial electrode 64 to position the second atrial electrode 152 at the os of the coronary sinus vein 160. Finally, the second defibrillation electrode 156 is spaced apart and proximal to the second atrial electrode 152 to position the second defibrillation electrode 156 in the right atrium chamber 70 or a major vein leading to the right atrium chamber 70 of the heart 32.

In an additional embodiment, the elongate body of the first atrial catheter 26 has a series of lateral deflections 162 between the proximal end 60 and distal end 62. The series of lateral deflections 162 are arcuate deflections that occur generally within a common plane along the extension of the longitudinal axis of the distal end 62 of the elongate body. In an additional embodiment, the series of lateral deflections 162 occur in opposite directions generally along the extension of a longitudinal axis of the distal end 62 of the elongate body.

In one embodiment, the series of lateral deflections 162 are created by imparting a mechanical bias into the electrically insulated conductors housed within the elongate body of the first atrial catheter 26 which create a semi-flexible/semi-rigid portion of the elongate body. In an alternative embodiment, the series of lateral deflections 162 are created by selecting polymers or altering the polymer structure used in constructing the elongate body of the catheter. In one embodiment, the series of lateral deflections 162 are intended to stabilize and secure the first atrial catheter 26 within the coronary sinus vein 160.

FIG. 5 shows one embodiment of a series of lateral deflections 162 where the elongate body of the first atrial catheter 26 has a first lateral deflection 164, a second lateral deflection 166, and a third lateral deflection 168 imparted into the elongate body of the first atrial catheter 26 that form a series of arcuate deflections. In FIG. 5, the first lateral deflection 164 first curves or bends away from the longitudinal axis of the first atrial catheter's elongate body. The first lateral deflection 164 upon reaching a first maximum deflection point 170 then begins to curve or bend back toward the long axis of the elongate body.

The second lateral deflection 166 begins as the first lateral deflection 164 returns the elongate body back to approximately the longitudinal axis. The second lateral deflection 166 is in the opposite direction of the first lateral deflection 164 in the plane of the series of lateral deflections 162. Once the second lateral deflection 166 reaches a second maximum deflection point 172 it begins to curve or bend back toward the longitudinal axis of the elongate body.

The third lateral deflection 168 begins as the second lateral deflection 166 returns the elongate body back to approximately the longitudinal axis. The third lateral deflection 168 then continues until it reaches a third maximum deflection point 174 and then begins to bend or curve back toward the longitudinal axis of the elongate body. The third lateral deflection 168 upon reaching the longitudinal axis of the elongate body curves or bends back to once again generally aligns with the longitudinal axis of the elongate body of the first atrial catheter 26.

In one embodiment, the first maximum deflection point 170 of the first lateral deflection 164 is spaced longitudinally from the third maximum deflection point 174 of the third lateral deflection 168 by distances in the range of 8 to 10 millimeters. In an additional embodiment, the first maximum deflection point 170 and the third maximum deflection point 174 of the first and the third lateral deflections are spaced horizontally from the second maximum deflection point 172 of the second lateral deflection in the range of 8 to 11 millimeters.

In a further embodiment, the first atrial electrode 64 is positioned on one of the series of lateral deflections 162 such that the series of lateral deflection 162 causes the first atrial electrode 64 to be mechanically biased into physical contact with the coronary sinus vein 160 of the heart 32. For example, the first atrial electrode 64 is positioned generally in the location of the second maximum deflection point 172 of the second lateral deflection 166 to allow the first atrial electrode 64 to contact the inner lumen of the coronary sinus vein 160.

The elongate body of the first atrial catheter 26 is made of extruded implantable polyurethane, silicone rubber or any other implantable flexible biocompatable polymer. The electrical leads 148, 150, 154 and 158 are made of MP35N alloy, or other commonly used electrical lead metal. The electrodes 64, 66, 152 and 156 are made of implantable metal such as platinum/iridium alloy or other commonly used electrode metal.

The first atrial catheter 26 also has a stylet passageway 176 which, in one embodiment, is created by the electrically insulated conductor 154, which has been coiled to create the stylet passageway 176. The stylet passageway 176 extends longitudinally in the elongate body from an inlet end located at the proximal end 60 to the distal end 62. The stylet passageway 176 is adapted to receive a guide stylet for stiffening and shaping the second atrial catheter 26 during insertion of the catheter into the heart 32. The coil of the stylet passageway 176 has sufficient flexibility to straighten due to the presence of a stylet, then return to the set shape after removal of the stylet.

Referring again to FIG. 4, the atrial cardioverter/defibrillator 22 is a programmable microprocessor-based system, with a microprocessor 110 and a memory 112, which contains parameters for various pacing and sensing modes. Microprocessor 110 includes means for communicating with an internal controller, in the form of an RF receiver/transmitter 114. This includes a wire loop antenna 116, whereby it may receive and transmit signals to and from an external controller 118. In this manner, programming commands or instructions are transferred to the microprocessor 110 of the atrial cardioverter/defibrillator 22 after implant. In one embodiment operating data is stored in memory 112 during operation. This data may be transferred to the external controller 118 for medical analysis.

In the atrial cardioverter/defibrillator 22 of FIG. 4, the first ventricle electrode 54 and the second ventricular electrode 56 are coupled to a sense amplifier 120, whose output is shown connected to an R-wave detector 122. These components serve to sense and amplify the QRS waves of the heart, and apply signals indicative thereof to the microprocessor 110. Among other things, microprocessor 110 responds to the R-wave detector 122 by providing pacing signals to a pace output circuit 124, as needed according to the programmed pacing mode. Pace output circuit 124 provides output pacing signals to terminals 102 and 104, which connect to the first ventricular electrode 54 and the second ventricular electrode 56, for ventricular pacing.

The second atrial electrode 152 and the first defibrillation electrode 66 are coupled to a sense amplifier 126, whose output is connected to a P-wave detector 128. These components serve to sense and amplify the P-waves of the cardiac cycle from the region of the left atrium chamber 72, and apply signals indicative thereof to the microprocessor 110. Among other things, microprocessor 110 responds to the atrial signals from the sense amplifier 126 applied to the P-wave detector 128 by providing pacing signals to the pace output circuit 124, as needed according to the programmed pacing mode. Pace output circuit 124 provides output pacing signals to terminals 106 and 108, which connect to the second atrial electrode 152 and the first defibrillation electrode 66, for normal atrial pacing and atrial pacing according to the present invention.

The first atrial electrode 64 and the second defibrillation electrode 156 are coupled to a sense amplifier 138, whose output is connected to the P-wave detector 128. These components serve to sense and amplify the P-waves of the cardiac cycle from the region of the right atrium chamber 70, and apply signals indicative thereof to the microprocessor 110. Among other things, microprocessor 110 responds to the atrial signals from the sense amplified 138 applied to the P-wave detector 128 by providing pacing signals to the pace output circuit 124, as needed according to the programmed pacing mode. Pace output circuit 124 provides output pacing signals to terminals 134 and 136, which connect to the first atrial electrode 64 and the second defibrillation electrode 156, for atrial pacing and atrial pacing according to the present invention.

The microprocessor 110 also responds to the cardiac signals sensed within the heart 32 using the catheters 24 and 26 by providing signals to a low-energy output circuit 130 to provide low-level cardioversion/defibrillation electrical energy to the heart as needed according to the method of the present invention. Power to the atrial cardioverter/ defibrillator 22 is supplied by an electrochemical battery 132 that is housed within the atrial cardioverter/defibrillator 22.

The electronic control circuitry 100 receives cardiac signals through the ventricle electrodes 54, 56, the first and second atrial electrodes 64, 152, and the first and second defibrillation electrodes 66, 156, and upon detecting an atrial fibrillation, first delivers a plurality of pacing pulses to the heart to convert the atrial fibrillation to a non-fibrillation atrial arrhythmia, such as atrial flutter or non-fibrillation supraventricular arrhythmia, and then delivers a low-energy atrial shock once the ventricular intervals stabilize.

In the embodiment shown in FIG. 3, the ventricular catheter 24 and the electronic control circuitry 100 are utilized for bipolar sensing of the ventricular R-wave intervals and the ventricular rate of the heart 32. Bipolar pacing is delivered between the first and the second ventricular electrodes 54 and 56. In an alternative embodiment, the ventricular catheter 24 has only a first ventricular electrode 54. Sensing ventricular R-wave intervals and ventricular rate is then accomplished through unipolar sensing between the first ventricular electrode 54 and an exposed electrically conductive portion of the implantable housing 34 which has been coupled to the sensing amplifier 120. Similarly, unipolar pacing is applied to the heart 32 between the first ventricular electrode 54 and the conductive implantable housing 34.

Referring again to FIG. 3, the first atrial catheter 26 and the electronic control circuitry 100 are utilized for bipolar sensing in two locations within the supraventricular region 68, where bipolar signals from the left atrium chamber 72 are sensed between the second atrial electrode 152 and the first defibrillation electrode 66 and bipolar signals from the right atrium chamber 70 are sensed between the first atrial electrode 64 and the second defibrillation electrode 156. For the first atrial catheter 26, bipolar pacing is delivered between the second atrial electrode 152 and the first defibrillation electrode 66, and between the first atrial electrode 64 and the second defibrillation electrode 156. In an alternative embodiment, unipolar pacing and sensing are provided from the first atrial catheter 26 between the second atrial electrode 152 and a conductive implantable housing 34 and/or the first atrial electrode 64 and the conductive implantable housing 34.

The atrial cardioverter/defibrillator 22 further includes the low-energy output circuit 130, which operates under the control of the microprocessor 110. The low-energy output circuit 130 is connected to the first and second defibrillation electrode terminals 108 and 136, which connects to the first and second defibrillation electrodes 66 and 156. In this manner, defibrillation pulses are delivered between the first defibrillation electrode 66 and the second defibrillation electrode 156 when called for by the microprocessor 110.

In an alternative embodiment, the implantable housing 34 of the system 20 is an additional defibrillation electrode, where the implantable housing 34 has an exposed electrically conductive surface electrically coupled to the low-energy output circuit 130, such that defibrillation pulses are being delivered between either defibrillation coil electrodes 66 or 156 and the implantable housing 34 of the system 20, or between any combination of the first defibrillation electrode 66 and/or second defibrillation electrode 156 and the implantable housing 34 of the system 20.

Figure 6:
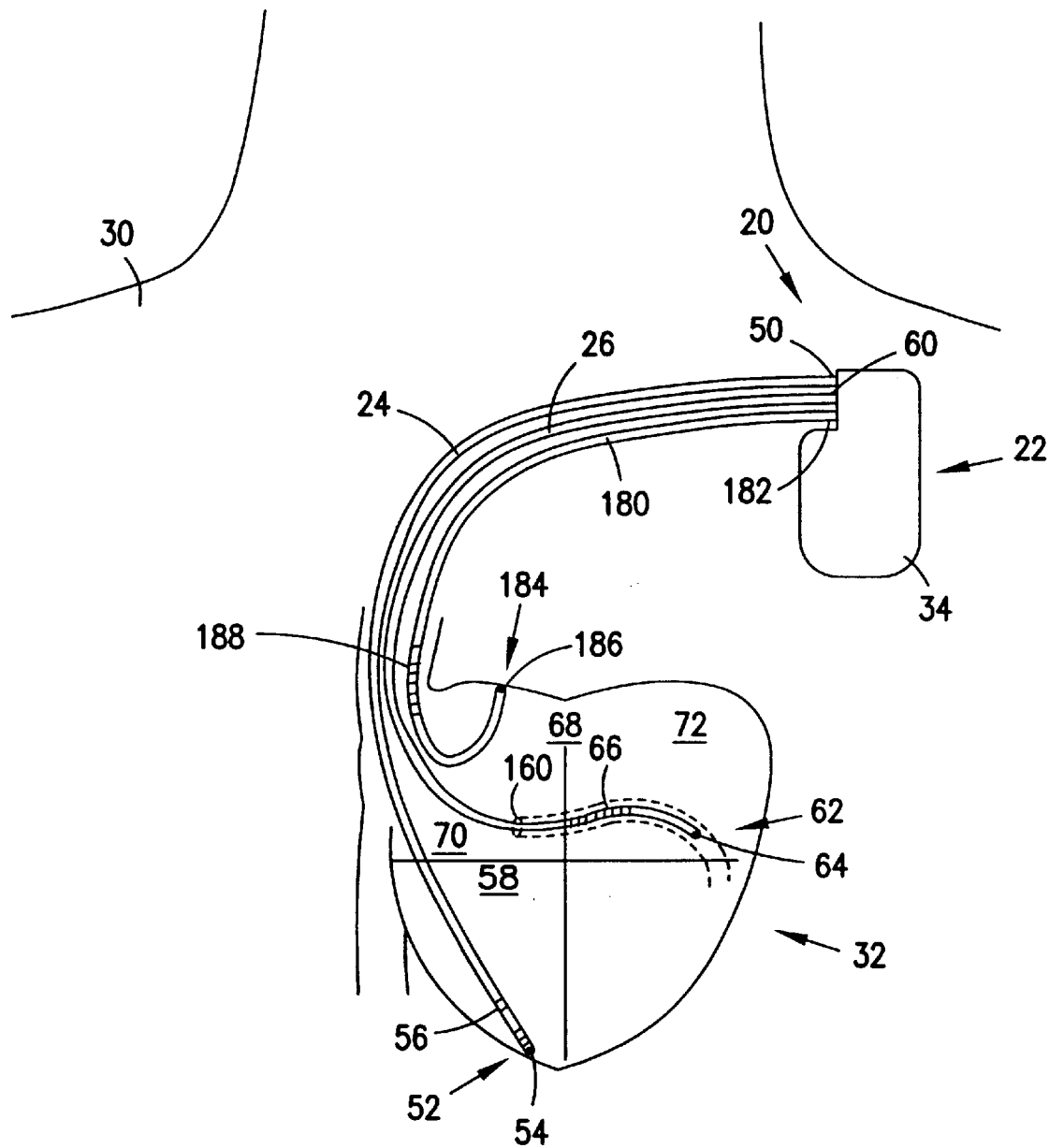
FIG. 6 is a schematic view of an atrial cardioverter/defibrillator with one embodiment of a first and second atrial catheter and a ventricular catheter implanted in a heart from which segments have been removed to show details.

Referring now to FIG. 6 of the drawings, there is shown an alternative embodiment of the system 20 further including a second atrial catheter 180. The system 20 is implanted in a human body 30 with portions of the ventricular catheter 24 and the first atrial catheter 26 and the second atrial catheter 180 inserted into a heart 32 to detect and analyze electric cardiac signals produced by the heart 32 and to provide electrical energy to the heart 32 under certain predetermined conditions to treat supraventricular tachyarrhythmias, including atrial fibrillation, of the heart 32.

A schematic of the atrial cardioverter/defibrillator 22 electronics is shown in FIG. 4. The atrial cardioverter/ defibrillator 22 comprises an implantable housing 34 which contains electronic control circuitry 100. The electronic control circuitry 100 includes terminals, labeled with reference numbers 102, 104, 106, 108, 134 and 136 for connection to electrodes attached to the surface of the ventricular catheter 24, and the first and second atrial catheters 26 and 180.

The ventricular catheter 24 is an endocardial lead adapted to be releasably attached to the implantable housing 34 of the system 20. The ventricular catheter 24 has an elongate body with a proximal end 50 and a distal end 52 and is shown as having a first ventricular electrode 54 located at, or adjacent, the distal end 52 of the ventricular catheter 24. In one embodiment, the first ventricular electrode 54 is a tip electrode positioned at the distal end 52 of the ventricular catheter 24. Alternatively, the first ventricular electrode 54 is an annular, or a semi-annular ring electrode positioned adjacent the distal end 52. The first ventricular electrode 54 is electrically connected to terminal 102 and to the electronic control circuitry 100 through an electrically insulated conductor provided within the elongate body of the ventricular catheter 24.

In an additional embodiment, the ventricular catheter 24 further includes a second ventricular electrode 56. The second ventricular electrode 56 is an annular, or a semi-annular ring electrode electrically connected to terminal 104 and to the electronic control circuitry 100 through an electrically insulated conductor provided within the elongate body of the ventricular catheter 24. The second ventricular electrode 56 is spaced apart and proximal from the first ventricular electrode 54 such that when the ventricular catheter 24 is positioned within the heart 32 the first ventricular electrode 54 and the second ventricular electrode 56 reside within a right ventricle 58 of the heart 32, with the first ventricular electrode 54 in an apex location within the right ventricle 58.

The first atrial catheter 26 is an endocardial lead adapted to be releasably attached to the implantable housing 34 of the system 20. The first atrial catheter 26 has an elongate body with a proximal end 60 and a distal end 62 and is shown as having a first atrial electrode 64 located at, or adjacent, the distal end 62. In one embodiment, the first atrial electrode 64 is a tip electrode positioned at the distal end 62 of the first atrial catheter 26. Alternatively, the first atrial electrode 64 is an annular, or a semi-annular ring electrode positioned adjacent the distal end 62. The first atrial electrode 64 is electrically connected to terminal 106 and to the electronic control circuitry 100 through an electrically insulated conductor provided within the elongate body of the first atrial catheter 26.

The first atrial catheter 26 also includes a first defibrillation electrode 66 which is connected to terminal 108 and to the electronic control circuitry 100 through an electrically insulated conductor provided within the elongate bony of the ventricular catheter 24. In one embodiment, the first defibrillation electrode 66 is a defibrillation coil electrode as are known in the art. The first defibrillation electrode 66 is spaced apart and proximal from the first atrial electrode 64 such that when the first atrial catheter 26 is positioned within the heart 32 the first atrial electrode 64 and the first defibrillation electrode 66 are positioned within a supraventricular region 68 of the heart 32. In one embodiment of the present system, the first atrial catheter 26 is positioned within the supraventricular region 68 of the heart 32 with the distal end 62 positioned within the coronary sinus vein 160 such that the first atrial electrode 64 is adjacent to and in physical contact with a portion of the left atrium chamber 72 of the heart 32 and the first defibrillation electrode 66 is positioned within the coronary sinus vein 160.

The second atrial catheter 180 is an endocardial lead adapted to be releasably attached to the implantable housing 34 of the system 20. The second atrial catheter 180 has an elongate body with a proximal end 182 and a distal end 184 and has at least a second atrial electrode located on the second atrial catheter 180. In one embodiment, FIG. 6 shows the second atrial catheter 180 as having a second atrial electrode 186 located at, or adjacent, the distal end 184. In one embodiment, the second atrial electrode 186 is a tip electrode positioned at the distal end 184 of the second atrial catheter 180. Alternatively, the second atrial electrode 186 is an annular, or a semi-annular ring electrode positioned adjacent the distal end 184. The second atrial electrode 186 is electrically connected to terminal 134 and to the electronic control circuitry 100 through an electrically insulated conductor provided within the elongate body of the second atrial catheter 180.

The second atrial catheter 180 also includes a second defibrillation electrode 188 which is connected to terminal 136 and to the electronic control circuitry 100 through an electrically insulated conductor provided within the elongate body of the second atrial catheter 180. In one embodiment, the second defibrillation electrode 188 is a defibrillation coil electrode as are known in the art. The second defibrillation electrode 188 is spaced apart and proximal from the second atrial electrode 186 such that when the second atrial catheter 180 is positioned within the heart 32 the second atrial electrode 186 and the second defibrillation electrode 188 are positioned within the right atrium chamber 70 of the heart 32 or a major vein leading to the right atrium chamber 70 of the heart 32. In one embodiment of the present system, the second atrial catheter 28 is positioned within the right atrium chamber 70 with the distal end 76 positioned within the right atrial appendage such that the second atrial electrode 186 make physical contact with the right atrium chamber 70 of the heart 32 and the second defibrillation electrode 188 is positioned within the right atrium and/or major vein leading to the right atrium chamber 70.

In the atrial cardioverter/defibrillator 22 of FIG. 4, the first ventricle electrode 54 and the second ventricular electrode 56 are coupled to a sense amplifier 120, whose output is shown connected to an R-wave detector 122. These components serve to sense and amplify the QRS waves of the heart, and apply signals indicative thereof to the microprocessor 110. Among other things, microprocessor 110 responds to the R-wave detector 122 by providing pacing signals to a pace output circuit 124, as needed according to the programmed pacing mode. Pace output circuit 124 provides output pacing signals to terminals 102 and 104, which connect to the first ventricular electrode 54 and the second ventricular electrode 56, for ventricular pacing.

The first atrial electrode 64 and the first defibrillation electrode 66 are coupled to a sense amplifier 126, whose output is connected to a P-wave detector 128. These components serve to sense and amplify the P-waves of the cardiac cycle from the region of the left atrium chamber 72, and apply signals indicative thereof to the microprocessor 110. Among other things, microprocessor 110 responds to the atrial signals from the sense amplifier 126 applied to the P-wave detector 128 by providing pacing signals to the pace output circuit 124, as needed according to the programmed pacing mode. Pace output circuit 124 provides output pacing signals to terminals 106 and 108, which connect to the first atrial electrode 64 and the first defibrillation electrode 66, for normal atrial pacing and atrial pacing according to the present invention.

The second atrial electrode 186 and the second defibrillation electrode 188 are coupled to a sense amplifier 138, whose output is connected to the P-wave detector 128. These components serve to sense and amplify the P-waves of the cardiac cycle from the region of the right atrium chamber 70, and apply signals indicative thereof to the microprocessor 110. Among other things, microprocessor 110 responds to the atrial signals from the sense amplified 138 applied to the P-wave detector 128 by providing pacing signals to the pace output circuit 124, as needed according to the programmed pacing mode. Pace output circuit 124 provides output pacing signals to terminals 134 and 136, which connect to the second atrial electrode 186 and the second defibrillation electrode 188, for atrial pacing and atrial pacing according to the present invention.

The microprocessor 110 also responds to the cardiac signals sensed within the heart 32 using the catheters 24, 26 and 180 by providing signals to a low-energy output circuit 130 to provide low-level cardioversion/defibrillation electrical energy to the heart as needed according to the method of the present invention. Power to the atrial cardioverter/defibrillator 22 is supplied by an electrochemical battery 132 that is housed within the atrial cardioverter/defibrillator 22.

The electronic control circuitry 100 receives cardiac signals through the ventricle electrodes 54, 56, the first and second atrial electrodes 64, 186, and the first and second defibrillation electrodes 66, 188, and upon detecting an atrial fibrillation, first delivers a plurality of pacing pulses to the heart to convert the atrial fibrillation to a non-fibrillation atrial arrhythmia, such as atrial flutter or non-fibrillation supraventricular arrhythmia, and then delivers a low-energy atrial shock once the ventricular intervals stabilize.

In the embodiment shown in FIG. 6, the first and second atrial catheters 26, 180 and the electronic control circuitry 100 are utilized for bipolar sensing in two locations within the supraventricular region 68, where bipolar signals from the left atrium chamber 72 are sensed between the first atrial electrode 64 and the first defibrillation electrode 66 and bipolar signals from the right atrium chamber 70 are sensed between the second atrial electrode 186 and the second defibrillation electrode 188. For the first atrial catheter 26, bipolar pacing is delivered between the first atrial electrode 64 and the first defibrillation electrode 66, and for the second atrial catheter 180 bipolar pacing is delivered between the second atrial electrode 186 and the second defibrillation electrode 188. In an alternative embodiment, unipolar pacing and sensing are provided from the first and/or the second atrial catheters 26, 180 between the first atrial electrode 64 and a conductive implantable housing 34 and/or the second atrial electrode 186 and the conductive implantable housing 34.

The atrial cardioverter/defibrillator 22 further includes the low-energy output circuit 130, which operates under the control of the microprocessor 110. The low-energy output circuit 130 is connected to the first and second defibrillation electrode terminals 108 and 136, which connects to the first and second defibrillation electrodes 66 and 188. In this manner, defibrillation pulses are delivered between the first defibrillation electrode 66 and the second defibrillation electrode 188 when called for by the microprocessor 110.

In an alternative embodiment, the implantable housing 34 of the system 20 is an additional defibrillation electrode, where the implantable housing 34 has an exposed electrically conductive surface electrically coupled to the low-energy output circuit 130, such that defibrillation pulses are being delivered between either defibrillation coil electrodes 66 or 188 and the implantable housing 34 of the system 20, or between any combination of the first defibrillation electrode 66 and/or second defibrillation electrode 188 and the implantable housing 34 of the system 20.

The ventricular catheter 24 and first a%id second atrial catheters 26 and 180 are releasably attached to and are separated from the atrial cardioverter/defibrillator 22 to facilitate inserting the catheters into the heart 32. The catheters are inserted transvenously through a cephalic or subclavian vein to position the distal ends of the catheters within the heart 32. The proximal ends of the catheters are then attached to the atrial cardioverter/defibrillator 22, where the proximal ends of the catheters are adapted to seal together with the terminals 102, 104, 106, 108, 134 and 136 of the atrial cardioverter/defibrillator 22 to thereby engage the individual electrode conductors and electrodes with the electronic control circuitry 100. The atrial cardioverter/defibrillator 22 of the system 20 is then positioned subcutaneously within the human body 30.

By way of further example of an embodiment of the system 20 having at least a second atrial electrode, it is considered to be within the scope of the present invention to have additional atrial pacing electrodes added to the system 20. In one embodiment, a plurality of pacing pulses can be applied at both a first atrial pacing location and at least two additional atrial pacing locations to convert the atrial fibrillation to non-fibrillation atrial arrhythmia. These additional atrial pacing sites can be endocardial or epicardial, where in one example the endocardial electrode can be located in the supraventricular region of the heart and the epicardial electrode can be located on the left atrial wall of the heart.

Figure 7:
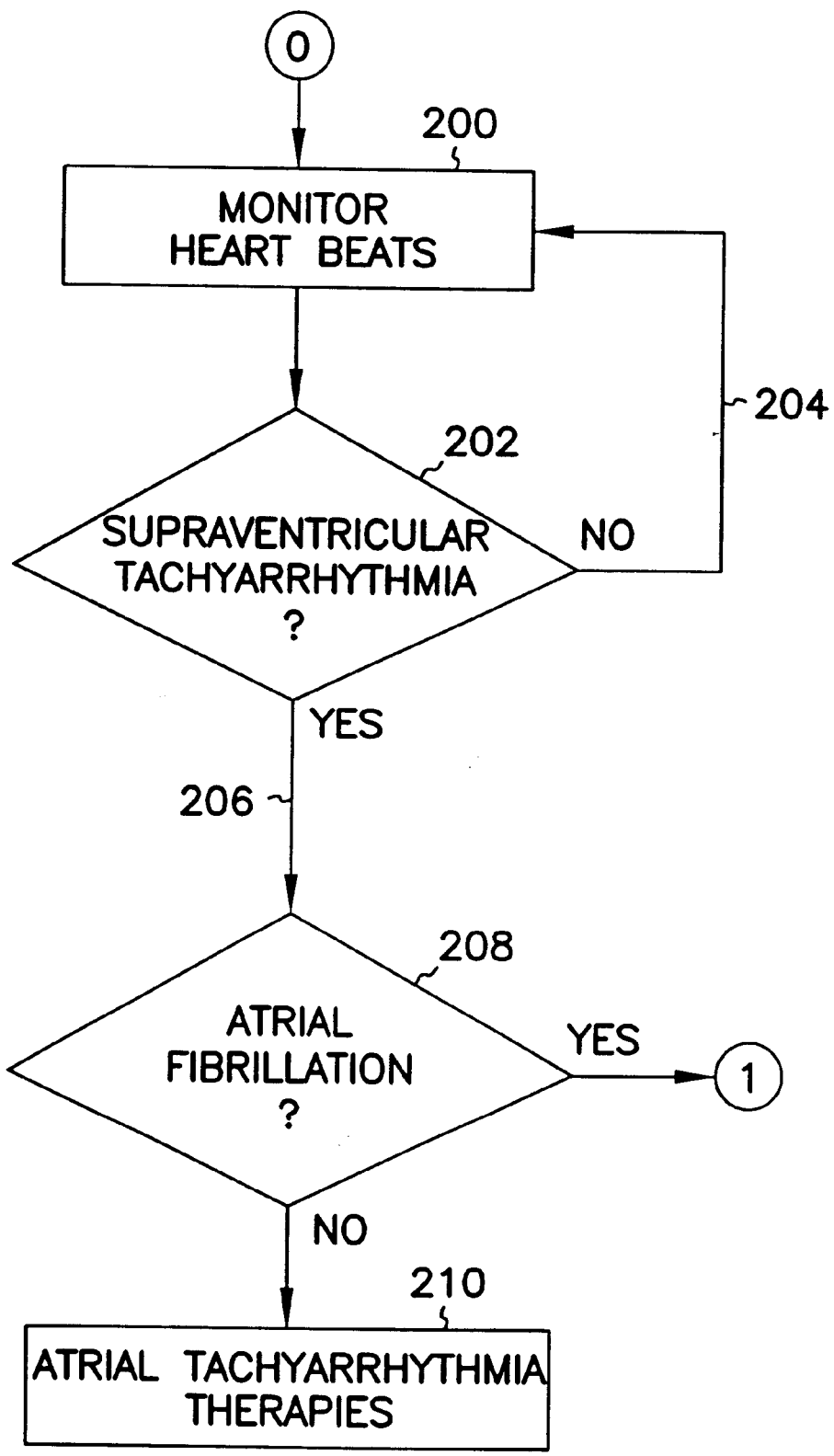
FIG. 7 is a flow diagram of an embodiment of the present invention.
Figure 8:
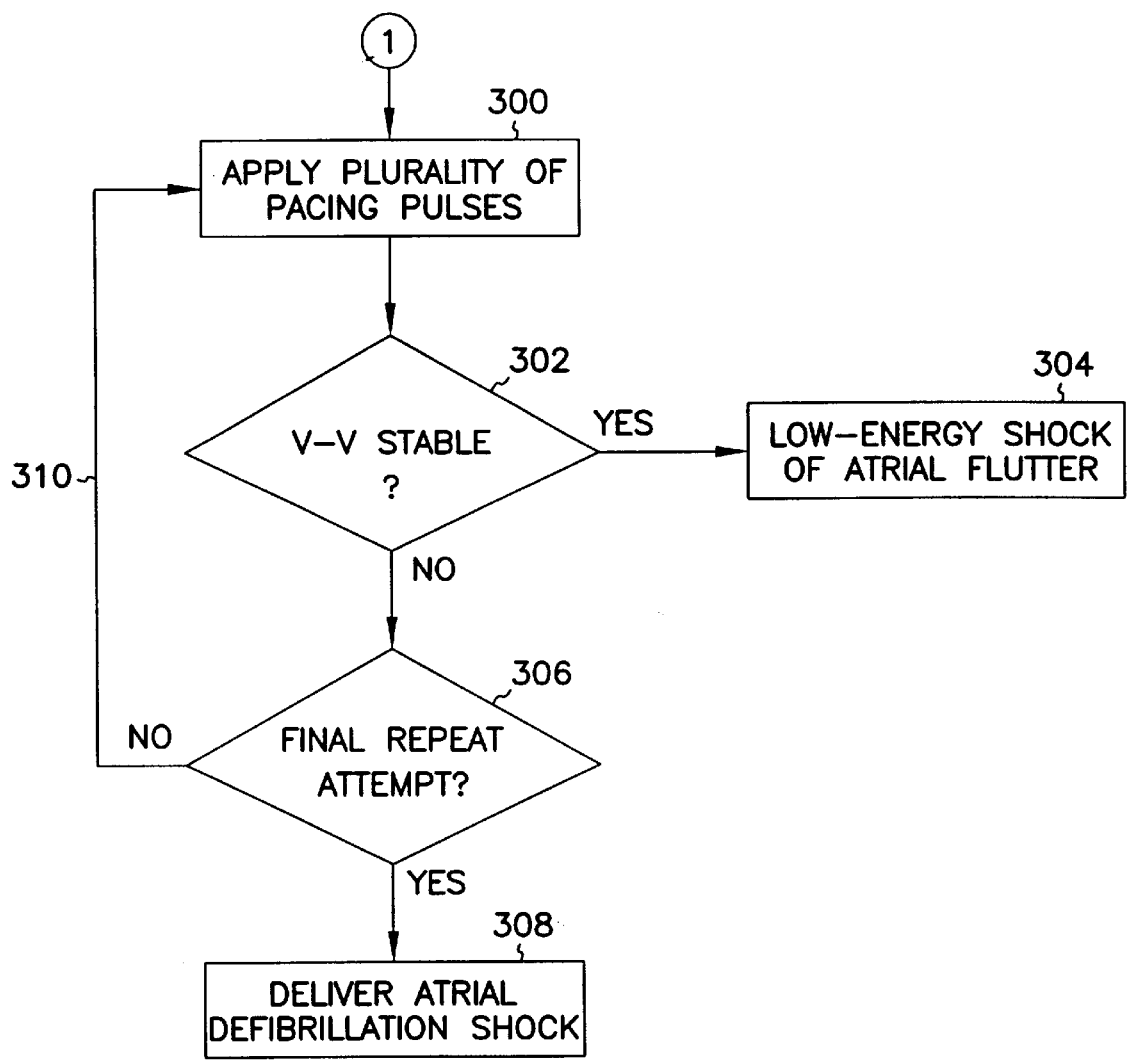
FIG. 8 is a flow diagram of an embodiment of the present invention.

FIGS. 7 and 8 illustrates the overall mode of operation of the system 20 in treating a heart experiencing an atrial fibrillation. In paced operation, the system 20 operates under programmed control to monitor the ventricular and atrial contractions occurring in the patient's heart. This is indicated by block 200 in FIG. 7. Monitoring of the cardiac rhythm is accomplished through the sense amps 120, 126 and 138, R-wave detector 122, and P-wave detector 128 which are all under the control of the microprocessor 110. Pacing may be administered as needed, depending upon the type of pacing functions provided in the atrial cardioverter/defibrillator 22.

Decision block 202 tests whether a supraventricular tachyarrhythmia has been detected. This is done through analysis of electrical cardiac signals from the heart under control of the microprocessor 110 and its stored programs. In one embodiment of the present invention, the atrial rate is used to determine the presence of a supraventricular tachyarrhythmia. If such condition is not detected, control branches via path 204 back to the heart beat monitor block 200, and the process continually repeats.

If, however, a supraventricular tachyarrhymia condition is detected at decision block 202, control passes via path 206 to decision block 208, which tests for the occurrence of atrial fibrillation. In one embodiment, atrial fibrillation is indicated when the atrial rate is greater than 250 beats per minute. Alternatively, atrial fibrillation is determined thought the analysis of detected cardiac electrogram signals, such as P-wave structure and/or P-wave intervals detected at the first atrial electrode 64 location and the second atrial electrode 152 location. If atrial fibrillation is not detected, control branches to block 210 for atrial tachyarrhythmia therapies.

If at block 208, an atrial fibrillation is detected, control branches to the atrial fibrillation therapies of FIG. 8, which first converts the atrial fibrillation to an atrial arrhythmia having a slower and more distinct cardiac rate and electrogram morphology. This newly created non-fibrillation atrial arrhythmia is more amenable to cardioversion/defibrillation, resulting in an increased probability of successfully converting the atria arrhythmia. Also, the cardioversion/defibrillation energy requirements are less than those required to cardiovert/defibrillate atrial fibrillation. This leads to a more patient acceptable manner of atrial fibrillation conversion.

As a way of determining when an atrial fibrillation has been converted to a non-fibrillation atrial arrhythmia, such as atrial flutter, by the plurality of pacing pulses, the system 20 monitors the intervals of ventricular contractions. In atrial fibrillation, the ventricular intervals are often rapid and unstable. It is theorized that this is the result of multiple wavelets, which make up the atrial fibrillation, impinging upon the AV-node. With such intense stimulation of the AV-node, the ventricular interval rate increases, and the stability of the intervals decreases due to the random and rapid nature of the atrial fibrillation wavelets.

Atrial fibrillation also requires a large amount of atrial tissue to sustain itself. In contrast, atrial flutter has far fewer wavelets than atrial fibrillation. By regionally capturing atrial tissue at one or more locations using pacing pulses of electrical energy, an atrial fibrillation may be converted to atrial flutter. This is because the number of wavelets to support the arrhythmia is proportional to the amount of atrial tissue available to support them. So as the amount of atrial tissue that is being controlled by the pacing pulses increases, less "uncontrolled" atrial tissue is available to sustain fibrillation, until finally the fibrillation is converted to some non-fibrillation atrial arrhythmia.

An indicator that the pacing pulses have converted an atrial fibrillation to atrial flutter, or another non-fibrillation atrial arrhythmia, is that the ventricular intervals are more likely to be stable. A stable ventricular interval is indicated when the standard deviation of ventricular intervals sensed during the delivery of the plurality of pacing pulses is less than a predetermined stability threshold value. Unstable ventricular intervals have deviation values that are equal to, or exceed, the predetermined stability threshold value.

Ventricular interval stability stems in part from the fact that atrial flutter usually occurs with an AV block, in which the block can have a contraction ratio of, for example, 2:1 or 3:1. Other ratios, however, exist which do not depart from the scope of the present invention. This distinction between ventricular instability during atrial fibrillation and ventricular stability during atrial flutter is utilized by the present invention to indicate when and if an atrial fibrillation has been converted by the plurality of pacing pulses, and to indicate when a cardioverting/defibrillating pulse of electrical energy is delivered to the atria to convert the heart to sinus rhythm. In one embodiment of the present invention, non-fibrillation atrial arrhythmia, such as an atrial flutter, is defined as having an atrial rate of between 150–250 beats per minute.

The beginning of the FIG. 8 flow chart, indicated by the symbol "1", is reached from the symbol "1" of the FIG. 8 flow chart. Referring now to FIG. 8, there is shown one embodiment of the present system where upon the occurrence or the detection of an atrial fibrillation condition, the system 20 treats the supraventricular region 68 of the heart 32 by applying a plurality of pacing pulses at a first atrial pacing location. The plurality of pacing pulses is delivered to the atria to convert the atrial fibrillation to a non-fibrillation atrial arrhythmia such as an atrial flutter. In one embodiment, the system 20 applies the plurality of pacing pulses across the second atrial electrode 152 located at the right atrial appendage. In another embodiment, the plurality of pacing pulses are delivered across the first atrial electrode 64 located adjacent to the left atrium chamber 72. Alternatively, the pacing pulses are delivered at other recognized supraventricular pacing locations, such as the os of the coronary sinus or the high right atrium.

The pacing pulse energy is a programmable value, with energy levels being set in the range of between approximately 10 to 15, 7 to 18, or 5 to 20 times the patient's diastolic threshold, where 10 times the patient's diastolic threshold is a suitable value. The diastolic threshold is a standard electrophysiological measurement to assess the minimum current or voltage needed to influence (capture) the tissue when it is in diastole. The pacing rate of the plurality of pacing pulses is also a programmable value which is set in a range of between approximately 120 to 160, 100 to 180, or 80 to 200 beats per minute. In an alternative embodiment, the plurality of pacing pulses has a pacing interval that is about 10 percent less than a patient's intrinsic cardiac interval. The plurality of pacing pulses are further delivered over a predetermined time of between approximately 30 to 40, 20 to 50, or 10 to 60 seconds.

As the plurality of electrical pacing pulses are being applied to the first atrial pacing location, the system 20 proceeds to step 302 and begins sensing and analyzing the ventricular intervals to determine their stability. As previously mentioned, a ventricular interval is the time between successive ventricular contractions, and is measured using the detected R-waves. Ventricular intervals are continuously averaged and a standard deviation calculated during the plurality of pacing pulses. The ventricular interval standard deviation is compared to the predetermined stability threshold value to determine if the sensed ventricular intervals are either stable or unstable. Ventricular intervals are stable if their standard deviation is less than the stability threshold value, and are unstable if their standard deviation is greater than or equal to the stability threshold value. The predetermined stability threshold value is within a range of between 25 to 35, 15 to 45, or 10 to 50 milliseconds.

During step 302, if the electronic control circuitry 100 of the system 20 determines that the heart 32 has entered a period of stable ventricular intervals (i.e., the ventricular intervals have become stable) control passes to step 304 where the system 20 proceeds to deliver a first level atrial shock to the heart. The first level atrial shock is a low-energy cardiovertion/defibrillation shock delivered to atria of the heart. In one embodiment, the low-energy cardiovertion/defibrillation shock is delivered between the first defibrillation electrode 66 placed in the coronary sinus vein 160 and the second defibrillation electrode 156 within the right atrium chamber 70 or major vein leading to the heart. Additionally, cardioverter/defibrillator 22 could be used as additional cardioversion/defibrillation electrodes to provide a variety of shocking patterns across the atria. Energy values for the first level atrial shock are programmable between 0.5 to 2, 0.4 to 3, or 0.3 to 5 joules.

In an alternative embodiment, after detecting an atrial fibrillation at block 208 the system 20 applies the plurality of pacing pulses at both a first atrial pacing location and a second atrial pacing location to convert the atrial fibrillation to a non-fibrillation atrial arrhythmia such as an atrial flutter. In one embodiment, the system 20 applies the plurality of pacing pulses across the first atrial electrode 64 located within the coronary sinus vein 160 adjacent to the left atrium chamber 72 and across the second atrial electrode 152 located at the right atrial appendage. In one embodiment, a predetermined time delay is provided between the pacing pulses delivered across the second atrial electrode 152 and the first atrial electrode 64. In this embodiment, a pacing pulse is first delivered across the second atrial electrode 152 to either a right atrium chamber 70 location or the coronary sinus vein 160 location. The pacing pulse delivered across the first atrial electrode 64 to the left atrium chamber 72 location is then postponed for the predetermined time delay, where the predetermined time delay is dependant upon the intrinsic intra-atrial conduction delay of the patient. In one embodiment, the predetermined time delay is a programmable time period in the range of between 10 to 100 milliseconds.

At step 302, the system 20 senses the ventricular intervals while the plurality of electrical pacing pulses are being applied to the first and second atrial pacing locations, and analyzes the ventricular intervals to determine ventricular stability, delivering the first level atrial shock to the heart during a period of stable ventricular intervals. If, however, the ventricular intervals do not become stable during the plurality of pacing pulses the method proceeds to step 306. At step 306 the system compares the number of attempts that have been made at converting the atria with a predetermined number of permitted attempts at converting the atrial fibrillation.

The system 20 is programmed to make two or more attempts, including a final repeat attempt, at converting an atrial fibrillation. For each attempt, the system repeats the aforementioned steps of applying a plurality of pacing pulses at one or more atrial pacing locations (e.g., the first and second atrial pacing electrodes), and sensing and analyzing the ventricular intervals for stability. If after a final repeat attempt a period of stable ventricular intervals is not determined during the analyzing step, the system proceeds to step 308 and delivers an atrial defibrillation shock to the heart.

The atrial defibrillation shock is a higher energy level shock than the low-energy level cardioversion shock and is intended to convert atrial fibrillation to sinus rhythm. For stable ventricular intervals the low-energy level cardioversion shock is delivered in the programmable range of between 0.1 to 1 Joule. If, however, the atrial defibrillation shock is delivered, it is delivered in the programmable range of between 1 to 6 Joules.

Referring back to step 306, in an alternative embodiment, if the plurality of pacing pulses at the first atrial pacing location has not resulted in ventricular stability and the system is not on a final repeat attempt, the system 20 returns to step 300 via path 310 and proceeds to repeat steps 300 and 302 by applying a plurality of pacing pulses at a second atrial pacing location to convert atrial fibrillation to a non-fibrillation atrial arrhythmia such as an atrial flutter. The second atrial location is a different pacing location than the first atrial location. So, in one embodiment, if the plurality of pacing pulses was delivered across the second atrial electrode 146, the subsequent delivery of a plurality of pacing pulses would be across the first atrial pacing electrode 64.

As the plurality of pacing pulses are being delivered across the second atrial electrode 152, the system 20 senses and analyzes ventricular intervals at step 302. Upon detecting a period of stable ventricular intervals, the system delivers a first level atrial shock to the heart during a period of stable ventricular intervals. If, however, the plurality of pacing pulses delivered across the second atrial electrode 152 fail to convert the atrial fibrillation to non-fibrillation atrial arrhythmia such as atrial flutter, the system 20 returns to step 300 via pathway 310 and proceeds to apply a plurality of pacing pulses at least once at both the first atrial pacing location and the second atrial pacing location to convert the atrial fibrillation to a non-fibrillation atrial arrhythmia such as atrial flutter. The system 20 at step 302 senses and analyzes ventricular intervals while the plurality of electrical pacing pulses are being applied to the first and the second atrial pacing locations to determine the stability of the ventricular intervals. Upon detecting a period of stable ventricular intervals, the system 20 delivers the first level atrial shock to the heart. If, however, the plurality of pacing pulses does not convert the atrial fibrillation to a non-fibrillation atrial arrhythmia, such as atrial flutter, during the final repeat attempt, the system 20 delivers an atrial defibrillation shock to the heart at step 308.

Alteratively, after unsuccessfully applying a plurality of pacing pulses at a first atrial pacing location, the system applies a plurality of pacing pulses at both the first atrial pacing location and a second atrial pacing location to convert the atrial fibrillation to a non-fibrillation atrial arrhythmia such as an atrial flutter. During the plurality of pacing pulses at both the first and second atrial pacing locations, the system senses and analyzes the ventricular intervals to determine the stability of the ventricular intervals. The system 20 delivers a first level atrial shock to the heart during a period of stable ventricular intervals.

If the attempt at converting the atria with the plurality of pacing pulses at both the first and second atrial pacing locations is unsuccessful, the system 20 repeats the step of applying a plurality of pacing pulses at the first and second atrial pacing locations until the final repeat attempt is complete, at which time if the system 20 is unable to convert the atrial fibrillation to a non-fibrillation atrial arrhythmia, such as an atrial flutter, the system 20 proceeds to deliver an atrial defibrillation shock to the heart at step 308.

What is claimed is:

1. A catheter, comprising:
   an elongate body having a peripheral surface, a proximal end and a distal end, and a first atrial electrode;
   a series of lateral deflections in the elongate body that occur generally within a common plane between the proximal end and distal end, where the series of lateral deflections has a first lateral deflection, a second lateral deflection, and a third lateral deflection, where the first lateral deflection curves away from the longitudinal axis of the elongate body and upon reaching a first maximum deflection point curves back towards the longitudinal axis, the second lateral deflection beginning as the first lateral deflection of the elongate body returns to approximately the longitudinal axis, where the second lateral deflection is in the opposite direction of the first lateral deflection, and upon reaching a second maximum deflection point curves back towards the longitudinal axis, and the third lateral deflection beginning as the second lateral deflection of the elongate body returns to approximately the longitudinal axis, where the third lateral deflection is in the opposite direction of the second lateral deflection, and upon reaching a third maximum deflection point curves back towards the longitudinal axis of the elongate body, and upon reaching the longitudinal axis, the elongate body curves back to generally align with the longitudinal axis of the elongate body, where the second lateral deflection has a magnitude greater than a magnitude of each of the first and third lateral deflections and where the first and third lateral deflections are directly adjacent the second lateral deflection, and where the first atrial electrode is located on one of the series of lateral deflections; and
   an electrically insulated conductor extending longitudinally within the elongate body from a contact end at the proximal end to the first atrial electrode.

2. The catheter of claim 1, where the first maximum deflection point is spaced longitudinally from the third maximum deflection point by a distance in the range of 8 to 10 millimeters.

3. The catheter of claim 1, including a first defibrillation electrode where the first defibrillation electrode is spaced longitudinally from the first atrial electrode along the peripheral surface and an electrically insulated conductor extending longitudinally within the elongate body from contact ends at the proximal end to the first defibrillation electrode.

4. The catheter of claim 3, including a second defibrillation electrode, where the second defibrillation electrode is spaced longitudinally from the first defibrillation electrode and the first atrial electrode along the peripheral surface, and an electrically insulated conductor extending longitudinally within the elongate body from contact ends at the proximal end to the second defibrillation electrode.

5. The catheter of claim 4, further including a second atrial pacing electrode at the distal end of the elongate body, where the first defibrillation electrode, the first atrial electrode and the second defibrillation electrode are spaced apart and longitudinally from the second atrial pacing electrode, and where the second atrial pacing electrode has an electrically insulated conductor extending longitudinally within the elongate body from a contact end at the proximal end to the second atrial pacing electrode.

6. The catheter of claim 4, where the first lateral deflection includes a first maximum deflection point, the second lateral deflection includes a second maximum deflection point and the third lateral deflection includes a third maximum deflection point, where the first maximum deflection point is spaced longitudinally from the third maximum deflection point by a distance in the range of 8 to 10 millimeters.

7. The catheter of claim 1, where the first atrial electrode is located on the second maximum deflection point of the second lateral deflection.

8. The catheter of claim 1, where the first maximum deflection point and the third maximum deflection point are spaced horizontally from the second maximum deflection point in a range of 8 to 11 millimeters.

9. A catheter, comprising:
an elongate body having a longitudinal axis, a first lateral deflection, a second lateral deflection and a third lateral deflection, where the first lateral deflection extends to a first side of the longitudinal axis, the second lateral deflection extends to a second side of the longitudinal axis, where second side is opposite the first side, and the third lateral deflection extends to the first side of the longitudinal axis, and where the first lateral deflection includes a first maximum deflection point, the second lateral deflection includes a second maximum deflection point and the third lateral deflection includes a third maximum deflection point, where the second lateral deflection has a magnitude greater than a magnitude of each of the first and third lateral deflections and where the first and third lateral deflections are directly adjacent the second lateral deflection;
a first atrial electrode located on one of the series of lateral deflections; and
an electrically insulated conductor extending longitudinally within the elongate body from a contact end to the first atrial electrode.

10. The catheter of claim 9, including a second defibrillation electrode, where the second defibrillation electrode is spaced longitudinally from the first defibrillation electrode and the first atrial electrode.

11. The catheter of claim 9, including a first defibrillation electrode, where the first defibrillation electrode is spaced longitudinally from the first atrial electrode.

12. The catheter of claim 9, where the first atrial electrode is located on the second maximum deflection point of the second lateral deflection.

13. The catheter of claim 9, where the first maximum deflection point and the third maximum deflection point are spaced horizontally from the second maximum deflection point in a range of 8 to 11 millimeters.

14. The catheter of claim 11, further including a second atrial pacing electrode, where the second atrial pacing electrode is at a distal end of the elongate body, where the first defibrillation electrode, the first atrial electrode and the second defibrillation electrode are spaced longitudinally from the second atrial pacing electrode, and where the second atrial pacing electrode has an electrically insulated conductor extending longitudinally within the elongate body from a contact end at the proximal end to the second atrial pacing electrode.

15. A catheter, comprising:
an elongate body having a peripheral surface, a proximal end and a distal end, and a first atrial electrode;
a series of lateral deflections in the elongate body that occur generally within a common plane between the proximal end and distal end, where the series of lateral deflections has a first lateral deflection, a second lateral deflection, and a third lateral deflection, where the first lateral deflection curves away from the longitudinal axis of the elongate body and upon reaching a first maximum deflection point curves back towards the longitudinal axis, the second lateral deflection beginning as the first lateral deflection of the elongate body returns to approximately the longitudinal axis, where the second lateral deflection is in the opposite direction of the first lateral deflection, and upon reaching a second maximum deflection point curves back towards the longitudinal axis, and the third lateral deflection beginning as the second lateral deflection of the elongate body returns to approximately the longitudinal axis, where the third lateral deflection is in the opposite direction of the second lateral deflection, and upon reaching a third maximum deflection point curves back towards the longitudinal axis of the elongate body, and upon reaching the longitudinal axis, the elongate body curves back to generally align with the longitudinal axis of the elongate body, and where the first atrial electrode is located on one of the series of lateral deflections; and
a first defibrillation electrode and a second defibrillation electrode, where the first defibrillation electrode is spaced longitudinally from the first atrial electrode along the peripheral surface, and the second defibrillation electrode is spaced longitudinally from the first defibrillation electrode and the first atrial electrode along the peripheral surface, and electrically insulated conductors extending longitudinally within the elongate body from contact ends at the proximal end to the first atrial electrode, the first defibrillation electrode, and the second defibrillation electrode.

16. The catheter of claim 15, where the first maximum deflection point is spaced longitudinally from the third maximum deflection point by a distance in the range of 8 to 10 millimeters.

17. The catheter of claim 15, further including a second atrial pacing electrode at the distal end of the elongate body, where the first defibrillation electrode, the first atrial electrode and the second defibrillation electrode are spaced apart and longitudinally from the second atrial pacing electrode, and where the second atrial pacing electrode has an electrically insulated conductor extending longitudinally within the elongate body from a contact end at the proximal end to the second atrial pacing electrode.

18. The catheter of claim 15, where the first atrial electrode is located on the second maximum deflection point of the second lateral deflection.

19. The catheter of claim 15, where the first maximum deflection point and the third maximum deflection point are spaced horizontally from the second maximum deflection point in a range of 8 to 11 millimeters.

20. A catheter, comprising:
an elongate body having a longitudinal axis, a first lateral deflection, a second lateral deflection and a third lateral deflection, where the first, second and third lateral deflections occur generally within a common plane when the catheter is located external a human body, the first lateral deflection being in a direction opposite the second lateral deflection with respect to the longitudinal axis and the second lateral deflection being in a direction opposite the third lateral deflection with respect to the longitudinal axis, and where the second lateral deflection begins as the first lateral deflection ends and the third lateral deflection beings as the second lateral deflection ends;
a first atrial electrode located on one of the series of lateral deflections;
a first defibrillation electrode and a second defibrillation electrode, where the first defibrillation electrode is spaced longitudinally from the first atrial electrode, and the second defibrillation electrode spaced longitudinally from the first defibrillation electrode and the first atrial electrode; and
electrically insulated conductors extending longitudinally within the elongate body from a contact end to the first atrial electrode the first defibrillation electrode and the second defibrillation electrode.

21. The catheter of claim 20, where the first lateral deflection includes a first maximum deflection point, the second lateral deflection includes a second maximum deflection point and the third lateral deflection includes a third maximum deflection point, where the first maximum deflection point is spaced longitudinally from the third maximum deflection point by a distance in the range of 8 to 10 millimeters.

22. The catheter of claim 21, where the first atrial electrode is located on the second maximum deflection point of the second lateral deflection.

23. The catheter of claim 21, where the first maximum deflection point and the third maximum deflection point are spaced horizontally from the second maximum deflection point in a range of 8 to 11 millimeters.

24. The catheter of claim 20, further including a second atrial pacing electrode, where the second atrial pacing electrode is at a distal end of the elongate body, where the first defibrillation electrode, the first atrial electrode and the second defibrillation electrode are spaced longitudinally from the second atrial pacing electrode, and where the second atrial pacing electrode has an electrically insulated conductor extending longitudinally within the elongate body from a contact end at the proximal end to the second atrial pacing electrode.

* * * * *

UNITED STATES PATENT AND TRADEMARK OFFICE
CERTIFICATE OF CORRECTION

PATENT NO.   : 6,430,449 B1
DATED        : August 6, 2002
INVENTOR(S)  : Hsu et al.

It is certified that error appears in the above-identified patent and that said Letters Patent is hereby corrected as shown below:

Column 22,
Line 56, delete "beings" and insert -- begins --, therefor.

Signed and Sealed this

Fifth Day of August, 2003

JAMES E. ROGAN
*Director of the United States Patent and Trademark Office*